(12) United States Patent
Sundermann et al.

(10) Patent No.: US 7,232,847 B2
(45) Date of Patent: Jun. 19, 2007

(54) 4-HYDROXYMETHYL-1-ARYL-CYCLOHEXYLAMINE COMPOUNDS

(75) Inventors: Bernd Sundermann, Aachen (DE); Hans Schick, Berlin (DE); Claudia Hinze, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/126,306

(22) Filed: May 11, 2005

(65) Prior Publication Data
US 2005/0267218 A1   Dec. 1, 2005

Related U.S. Application Data

(63) Continuation of application No. PCT/EP03/12312, filed on Nov. 5, 2003.

(30) Foreign Application Priority Data
Nov. 12, 2002   (DE) ............... 102 52 872
Nov. 14, 2002   (DE) ............... 102 53 323

(51) Int. Cl.
*A61K 31/13*   (2006.01)
*C07C 211/34*   (2006.01)
(52) U.S. Cl. .............. 514/740; 514/741; 564/462
(58) Field of Classification Search ........... 514/740, 514/741; 564/462
See application file for complete search history.

(56) References Cited

U.S. PATENT DOCUMENTS 4,115,589 A   9/1978   Lednicer 5,968,737 A * 10/1999 Ali-Osman et al. ........... 435/6

FOREIGN PATENT DOCUMENTS

WO   WO 99/36421         7/1998
WO   WO 02/090317 A1    11/2002

OTHER PUBLICATIONS

Gurjar et al. "Total synthesis of cis and trans-hydroxyglimepride: active metabolite of glimepiride" Tetrahedron Letters 2003, vol. 44, pp. 4853-4855.*
Abdulla and Smith, J. Neurosci. 18, 1998, p. 9685-9694.
Ardati et al., Mol. Pharmacol., 51, 1997, p. 816-824.
Calo et al., Br. J. Pharmacol., 129, 2000, 1261-1283.
Jenck et al., Proc. Natl. Acad. Sci. USA 94, 1997, 14854-14858.
King et al., Neurosci. Lett., 223, 1997, 113-116.
Lednicer et al., J. Med. Chem., 23, 1980, 424-430.
Manabe et al., Nature, 394, 1997, p. 577-581.
Meunier et al., Nature 377, 1995, p. 532-535.
Mogil et al., Neuroscience 75, 1996, p. 333-337.
Nishi et al., EMBO J., 16, 1997, p. 1858 1864.
Paquette, et al., Tetrahedron Letters, 34, 1993, p. 3523-3526.
Reinscheid et al., Science 270, 1995, p. 792-794.

* cited by examiner

*Primary Examiner*—Kamal A. Saeed
*Assistant Examiner*—Joseph R. Kosack
(74) *Attorney, Agent, or Firm*—Crowell & Moring LLP

(57) ABSTRACT

The invention relates to 4-hydroxymethyl-1-aryl-cyclohexylamine compounds, methods for their production, pharmaceutical formulations containing such compounds and the use of 4-hydroxymethyl-1-aryl-cyclohexylamine derivatives for producing medicines which are useful, for example for treating pain. Related methods of treatment are also provided.

37 Claims, No Drawings

4-HYDROXYMETHYL-1-ARYL-CYCLOHEXYLAMINE COMPOUNDS

CROSS REFERENCE TO RELATED APPLICATIONS

This application is a continuation of International Patent Application No. PCT/EP2003/012312, filed Nov. 5, 2003, designating the United States of America, and published in German as WO 2004/043902 A1, the entire disclosure of which is incorporated herein by reference. Priority is claimed based on Federal Republic of Germany Patent Application Nos. 102 52 872.1, filed Nov. 12, 2002, and 102 53 323.7, filed Nov. 14, 2002.

FIELD OF THE INVENTION

The present invention relates to 4-hydroxymethyl-1-aryl-cyclohexylamine compounds, to processes for their preparation, to pharmaceutical formulations containing said compounds and to the use of 4-hydroxymethyl-1-arylcyclohexylamine compounds for the preparation of pharmaceutical formulations and related methods of treatment.

BACKGROUND OF THE INVENTION

The heptadecapeptide nociceptin is an endogenous ligand of the ORL1 receptor (ORL=Opioid-Receptor-Like)(Meunier et al., Nature 377, 1995, pp 532-535), which belongs to the family of the opioid receptors, is found in many regions of the brain and spinal cord and has a high affinity for the ORL1 receptor. The ORL1 receptor is homologous to the μ, κ and δ opioid receptors and the amino acid sequence of the nociceptin peptide has a strong similarity to those of the known opioid peptides. The receptor activation induced by nociceptin leads to an inhibition of adenylate cyclase via coupling with $G_{i/o}$ proteins (Meunier et al., Nature 377, 1995, pp 532-535).

After intercerebroventricular administration, the nociceptin peptide displays a pronociceptive and hyperalgesic activity in various animal models (Reinscheid et al., Science 270, 1995, pp 792-794). These findings can be explained as an inhibition of stress-induced analgesia (Mogil et al., Neuroscience 75, 1996, pp 333-337). In this connection it has also been possible to detect an anxiolytic activity of nociceptin (Jenck et al., Proc. Natl. Acad. Sci. USA 94, 1997, 14854-14858).

On the other hand, it has also been possible to show an antinociceptive effect of nociceptin in various animal models, especially after intrathecal administration. Nociceptin has an antinociceptive action in various pain models, for example in the mouse tail flick test (King et al., Neurosci. Lett. 223, 1997, 113-116). In neuropathic pain models, it has likewise been possible to detect an antinociceptive action of nociceptin which is of particular interest inasmuch as the efficacy of nociceptin increases after the axotomy of spinal nerves. This is in contrast to the classical opioids, whose efficacy decreases under these conditions (Abdulla and Smith, J. Neurosci. 18, 1998, pp 9685-9694).

The ORL1 receptor also participates in the regulation of other physiological and pathophysiological processes. These include, inter alia, learning and memorization (Manabe et al., Nature 394, 1997, pp 577-581), hearing acuity (Nishi et al., EMBO J. 16, 1997, pp 1858-1864) and numerous other processes. A survey by Calo et al. (Br. J. Pharmacol. 129, 2000, 1261-1283) gives a summary of the indications or biological processes in which the ORL1 receptor plays or very probably might play a role. The following are mentioned, inter alia: analgesia, stimulation and regulation of ingestion, effect on μ agonists such as morphine, treatment of withdrawal symptoms, reduction of the addiction potential of opioids, anxiolysis, modulation of motor activity, memory disorders, epilepsy, modulation of the release of neurotransmitters, especially glutamate, serotonin and dopamine, and hence neurodegenerative diseases, influence on the cardiovascular system, triggering of an erection, diuresis, antinatriuresis, electrolyte metabolism, arterial blood pressure, water retention diseases, intestinal motility (diarrhoea), relaxing effects on the respiratory tract, and micturition reflex (urinary incontinence). Said survey further discusses the use of agonists and antagonists as anoretics, analgesics (also in coadministration with opioids) or nootropics.

The possible applications of compounds that bind to the ORL1 receptor and activate or inhibit it are correspondingly diverse. Apart from this receptor, opioid receptors such as the μ receptor and other subtypes play a major role in the precise area of pain therapy, but also in other indications among those mentioned. Accordingly, it is advantageous if a compound is also active at these opioid receptors.

SUMMARY OF THE INVENTION

One object of certain embodiments of the present invention is to provide pharmaceutical formulations which are active on the nociceptin/ORL1 receptor system and hence are suitable as pharmaceutical formulations especially for the treatment of the various diseases associated with this system according to the state of the art, or for use in the indications mentioned therein.

The invention therefore provides 4-hydroxymethyl-1-arylcyclohexylamine derivatives of general formula I:

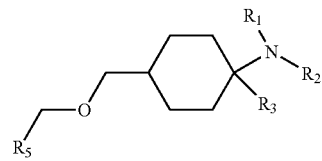

in which $R^1$ and $R^2$ independently of one another are H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted, or the radicals $R^1$ and $R^2$ together form a ring and are $CH_2CH_2OCH_2CH_2$, $CH_2CH_2NR^6CH_2CH_2$ or $(CH_2)_{3-6}$, $R^6$ being H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted;

$R^3$ is $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is unsubstituted, monosubstituted or polysubstituted; or aryl, $C_{3-8}$-cycloalkyl or heteroaryl bonded via a saturated or unsaturated, branched or unbranched and substituted or unsubstituted $C_{1-4}$-alkyl group, each of which is unsubstituted, monosubstituted or polysubstituted; and $R^5$ is $C_{3-8}$-cycloalkyl, aryl or heteroaryl, each of which is unsubstituted, monosubstituted or polysubstituted; or —$CH_2R^{12}$, —$CH_2$—$CH_2R^{12}$ or —$CH_2$—$CH_2$—$CH_2R^{12}$, $R^{12}$ being $C_{3-8}$-cycloalkyl, aryl or heteroaryl, each of which is unsubstituted, monosubstituted or polysubstituted, optionally in the form of their racemates or pure stereoisomers, especially enantiomers or diastereoisomers, or in the form of mixtures of the stereoisomers, especially enantiomers or diastereoisomers, in any desired mixing ratio; and in the form of their acids or bases or in the form of their salts, especially physiologically acceptable salts or salts of physiologically acceptable acids or cations, or in the form of their solvates, especially hydrates.

All these compounds according to the invention exhibit a good binding to the ORL1 receptor, but also to other opiate receptors.

In terms of the present invention, alkyl or cycloalkyl radicals are understood as meaning saturated and unsaturated (but not aromatic), branched, unbranched and cyclic hydrocarbons which can be unsubstituted, monosubstituted or polysubstituted. $C_{1-2}$-alkyl is $C_1$- or $C_2$-alkyl, $C_{1-3}$-alkyl is $C_1$-, $C_2$- or $C_3$-alkyl, $C_{1-4}$-alkyl is $C_1$-, $C_2$-, $C_3$- or $C_4$-alkyl, $C_{1-5}$-alkyl is $C_1$-, $C_2$-, $C_3$-, $C_4$- or $C_5$-alkyl, $C_{1-6}$-alkyl is $C_1$-, $C_2$-, $C_3$-, $C_4$-, $C_5$- or $C_6$-alkyl, $C_{1-7}$-alkyl is $C_1$-, $C_2$-, $C_3$-, $C_4$-, $C_5$-, $C_6$- or $C_7$-alkyl, $C_{1-8}$-alkyl is $C_1$-, $C_2$-, $C_3$-, $C_4$-, $C_5$-, $C_6$-, $C_7$- or $C_8$-alkyl, $C_{1-10}$-alkyl is $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl is $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. Also, $C_{3-4}$-cycloalkyl is $C_3$- or $C_4$-cycloalkyl, $C_{3-5}$-cycloalkyl is $C_3$-, $C_4$- or $C_5$-cycloalkyl, $C_{3-6}$-cycloalkyl is $C_3$-, $C_4$-, $C_5$-, or $C_6$-cycloalkyl, $C_{3-7}$-cycloalkyl is $C_3$-, $C_4$-, $C_5$-, $C_6$- or $C_7$-cycloalkyl, $C_{3-8}$-cycloalkyl is $C_3$-, $C_4$-, $C_5$-, $C_6$-, $C_7$- or $C_8$-cycloalkyl, $C_{4-5}$-cycloalkyl is $C_4$- or $C_5$-cycloalkyl, $C_{4-6}$-cycloalkyl is $C_4$-, $C_5$- or $C_6$-cycloalkyl, $C_{4-7}$-cycloalkyl is $C_4$-, $C_5$-, $C_6$- or $C_7$-cycloalkyl, $C_{5-6}$-cycloalkyl is $C_5$- or $C_6$-cycloalkyl and $C_{5-7}$-cycloalkyl is $C_5$-, $C_6$- or $C_7$-cycloalkyl. The term "cycloalkyl" also includes saturated cycloalkyls in which one or 2 carbon atoms are replaced by a heteroatom S, N or O. In particular, however, the term "cycloalkyl" also includes monounsaturated or polyunsaturated cycloalkyls, preferably monounsaturated cycloalkyls, without a heteroatom in the ring, provided the cycloalkyl is not an aromatic system. Preferably, the alkyl or cycloalkyl radicals are methyl, ethyl, vinyl (ethenyl), propyl, allyl (2-propenyl), 1-propynyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl or cyclooctyl, or adamantyl, $CHF_2$, $CF_3$ or $CH_2OH$, as well as pyrazolinone, oxopyrazolinone, 1,4-dioxane or dioxolane.

According to the present invention, the term "substituted" in connection with alkyl and cycloalkyl—unless expressly defined otherwise—is understood as meaning the substitution of at least one (or optionally several) hydrogen radical(s) by F, Cl, Br, I, $NH_2$, SH or OH, "polysubstituted" or "substituted" in the case of polysubstitution being understood as meaning that the substitution takes place several times on different atoms or on the same atoms with the same or different substituents, for example trisubstituted on the same C atom as in the case of $CF_3$, or at different sites as in the case of —CH(OH)—CH=CH—$CHCl_2$. Particularly preferred substituents here are F, Cl and OH. As regards cycloalkyl, the hydrogen radical can also be replaced by $OC_{1-3}$-alkyl or $C_{1-3}$-alkyl (in each case monosubstituted, polysubstituted or unsubstituted), especially methyl, ethyl, n-propyl, i-propyl, $CF_3$, methoxy or ethoxy.

The term "$(CH_2)_{3-6}$" is understood as meaning —$CH_2$—$CH_2$—$CH_2$—,
—$CH_2$—$CH_2$—$CH_2$—$CH_2$—, —$CH_2$—$CH_2$—$CH_2$—$CH_2$—$CH_2$— and
—$CH_2$—$CH_2$—$CH_2$—$CH_2$—$CH_2$—$CH_2$—, "$(CH_2)_{1-4}$" is understood as meaning —$CH_2$—, —$CH_2$—$CH_2$—, —$CH_2$—$CH_2$—$CH_2$— and —$CH_2$—$CH_2$—$CH_2$—$CH_2$—, "$(CH_2)_{4-5}$" is understood as meaning —$CH_2$—$CH_2$—$CH_2$—$CH_2$— and
—$CH_2$—$CH_2$—$CH_2$—$CH_2$—$CH_2$—, etc.

An aryl radical is understood as meaning a ring system having at least one aromatic ring but no heteroatoms, even in only one of the rings. Examples are phenyl, naphthyl, fluoranthenyl, fluorenyl, tetralinyl or indanyl radicals, especially 9H-fluorenyl or anthracenyl radicals, which can be unsubstituted, monosubstituted or polysubstituted.

A heteroaryl radical is understood as meaning a heterocyclic ring system having at least one unsaturated ring and containing one or more heteroatoms from the group comprising nitrogen, oxygen and/or sulfur, it also being possible for said ring system to be monosubstituted or polysubstituted. The following may be listed as examples of heteroaryl radicals: furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

"Substituted" in connection with aryl and heteroaryl is understood as meaning substitution of the aryl or heteroaryl with $R^{22}$, $OR^{22}$, halogen, preferably F and/or Cl, $CF_3$, CN, $NO_2$, $NR^{23}R^{24}$, $C_{1-6}$-alkyl (saturated), $C_{1-6}$-alkoxy, $C_{3-8}$-cycloalkoxy, $C_{3-8}$-cycloalkyl or $C_{2-6}$-alkylene.

In these definitions, the radical $R^{22}$ is H, a $C_{1-10}$-alkyl radical, preferably a $C_{1-6}$-alkyl radical, an aryl or heteroaryl radical or an aryl or heteroaryl radical bonded via a saturated or unsaturated $C_{1-3}$-alkyl, it being impossible for these aryl and heteroaryl radicals themselves to be substituted by aryl or heteroaryl radicals, the radicals $R^{23}$ and $R^{24}$, which are identical or different, are H, a $C_{1-10}$-alkyl radical, preferably a $C_{1-6}$-alkyl radical, an aryl or heteroaryl radical or an aryl or heteroaryl radical bonded via a saturated or unsaturated $C_{1-3}$-alkyl, it being impossible for these aryl and heteroaryl radicals themselves to be substituted by aryl or heteroaryl radicals, or the radicals $R^{23}$ and $R^{24}$ together are $CH_2CH_2OCH_2CH_2$, $CH_2CH_2NR^{25}CH_2CH_2$ or $(CH_2)_{3-6}$, and the radical $R^{25}$ is H, a $C_{1-10}$-alkyl radical, preferably a $C_{1-6}$-alkyl radical, an aryl or heteroaryl radical or an aryl or heteroaryl radical bonded via a saturated or unsaturated $C_{1-3}$-alkyl, it being impossible for these aryl and heteroaryl radicals themselves to be substituted by aryl or heteroaryl radicals.

The term "salt" is understood as meaning any form of the active substance according to the invention in which said active substance assumes an ionic form, or is charged and coupled with a counterion (a cation or anion), or is present in solution. Also included here are complexes of the active substance with other molecules and ions, especially complexes that are complexed via ionic interactions. In particular (and this is also a preferred embodiment of the present invention), said salts are understood as meaning physiologically acceptable salts, especially physiologically acceptable salts with cations or bases and physiologically acceptable salts with anions or acids, or salts formed with a physiologically acceptable acid or a physiologically acceptable cation.

In terms of the present invention, the expression "physiologically acceptable salts with anions or acids" is understood as meaning salts of at least one of the compounds according to the invention—usually protonated, for example on the nitrogen—as a cation with at least one anion, which are physiologically acceptable, especially when administered to a human and/or mammal. In terms of the present invention, they are understood in particular as meaning salts formed with a physiologically acceptable acid, i.e. salts of the active substance in question with inorganic or organic acids which are physiologically acceptable, especially when administered to a human and/or mammal. Examples of physiologically acceptable salts of specific acids are those of hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-benzo[d]isothiazol-3-one (saccharin acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt and the citrate salt are particularly preferred.

In terms of the present invention, the expression "salts formed with a physiologically acceptable acid" is understood as meaning salts of the active substance in question with inorganic or organic acids which are physiologically acceptable, especially when administered to a human and/or mammal. The hydrochloride and the citrate are particularly preferred. Examples of physiologically acceptable acids are hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-benzo[d]isothiazol-3-one (saccharin acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid.

In terms of the present invention, the expression "physiologically acceptable salts with cations or bases" is understood as meaning salts of at least one of the compounds according to the invention—usually a (deprotonated) acid—as an anion with at least one, preferably inorganic cation, which are physiologically acceptable, especially when administered to a human and/or mammal. Particularly preferred salts are those of alkali metals and alkaline earth metals as well as those of $NH_4^+$, especially monosodium or disodium salts, monopotassium or dipotassium salts, magnesium salts or calcium salts.

In terms of the present invention, the expression "salts formed with a physiologically acceptable cation" is understood as meaning salts of at least one of the compounds in question, as an anion with at least one inorganic cation which is physiologically acceptable, especially when administered to a human and/or mammal.

Particularly preferred salts are those of alkali metals and alkaline earth metals as well as those of $NH_4^+$, especially monosodium or disodium salts, monopotassium or dipotassium salts, magnesium salts or calcium salts.

In terms of the present invention, preferred 4-hydroxymethyl-1-arylcyclohexylamine derivatives are those in which
$R^1$ and $R^2$ independently of one another are H; or $C_{1-8}$-alkyl which is saturated or unsaturated, branched or unbranched and monosubstituted, polysubstituted or unsubstituted,
or the radicals $R^1$ and $R^2$ together form a ring and are $CH_2CH_2OCH_2CH_2$, $CH_2CH_2NR^6CH_2CH_2$ or $(CH_2)_{3-6}$,
$R^6$ being H; or $C_{1-8}$-alkyl which is saturated or unsaturated, branched or unbranched and monosubstituted, polysubstituted or unsubstituted,
and preferably
$R^1$ and $R^2$ independently of one another are H; or $C_{1-4}$-alkyl which is saturated or unsaturated, branched or unbranched and monosubstituted, polysubstituted or unsubstituted, it being impossible for both $R^1$ and $R^2$ to be H, or the radicals $R^1$ and $R^2$ together form a ring and are $(CH_2)_{4-5}$.

Particularly preferred 4-hydroxymethyl-1-arylcyclohexylamine derivatives are those in which
$R^1$ and $R^2$ independently of one another are methyl or ethyl, or the radicals $R^1$ and $R^2$ together form a ring and are $(CH_2)_5$,
or $R^1$ and $R^2$ independently of one another are $CH_3$ or H, $R^1$ and $R^2$ not being H simultaneously.

Other preferred 4-hydroxymethyl-1-arylcyclohexylamine derivatives in terms of the present invention are those in which
$R^3$ is $C_{3-8}$-cycloalkyl, aryl or heteroaryl, each of which is unsubstituted, monosubstituted or polysubstituted; or aryl, $C_{3-8}$-cycloalkyl or heteroaryl bonded via a saturated or unsaturated, unbranched and substituted or unsubstituted $C_{1-2}$-alkyl group, each of which is unsubstituted, monosubstituted or polysubstituted,
preferably
$R^3$ is cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, each of which is unsubstituted, monosubstituted or polysubstituted; or a $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated unbranched $C_{1-2}$-alkyl group, each of which is unsubstituted, monosubstituted or polysubstituted,
and especially
$R^3$ is phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, each of which is unsubstituted, monosubstituted or polysubstituted; or phenyl, furyl or thiophenyl bonded via a saturated unbranched $C_{1-2}$-alkyl group, each of which is unsubstituted, monosubstituted or polysubstituted.

Particularly preferred 4-hydroxymethyl-1-arylcyclohexylamine derivatives are those in which $R^3$ is phenyl, thiophenyl, pyridyl or benzyl, each of which is substituted or unsubstituted, phenyl being very particularly preferred.

Other preferred 4-hydroxymethyl-1-arylcyclohexylamine derivatives are those in which $R^5$ is $C_{3-8}$-cycloalkyl, aryl or heteroaryl, each of which is unsubstituted, monosubstituted or polysubstituted,
preferably
$R^5$ is cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each of which is unsubstituted, monosubstituted or polysubstituted,
and especially
$R^5$ is cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each of which is unsubstituted, monosubstituted or polysubstituted.

Very particularly preferably, $R^5$ is selected from phenyl and indolyl, each of which is unsubstituted, monosubstituted or polysubstituted, particular preference being given, according to the invention, to unsubstituted phenyl or indolyl, phenyl monosubstituted in the para position by methyl, methoxy, chlorine, fluorine or $CF_3$, or indolyl substituted in the 5-position by methyl, methoxy, chlorine, fluorine or $CF_3$.

Other preferred 4-hydroxymethyl-1-arylcyclohexylamine derivatives are those in which $R^5$ is —$CH_2R^{12}$, —$CH_2$—$CH_2R^{12}$ or —$CH_2$—$CH_2$—$CH_2R^{12}$,
preferably
$R^5$ is —$CH_2R^{12}$ or —$CH_2$—$CH_2R^{12}$,
and especially
$R^5$ is —$CH_2R^{12}$,
$R^{12}$ being $C_{3-8}$-cycloalkyl, aryl or heteroaryl, each of which is unsubstituted, monosubstituted or polysubstituted,
preferably
$R^{12}$ being cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each of which is unsubstituted, monosubstituted or polysubstituted,
and especially
$R^{12}$ being cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each of which is unsubstituted, monosubstituted or polysubstituted.

Very particularly preferred 4-hydroxymethyl-1-arylcyclohexylamine derivatives are those of the group comprising (4-benzyloxymethyl-1-phenylcyclohexyl)dimethylamine hydrochloride, less polar diastereoisomer,
(4-benzyloxymethyl-1-phenylcyclohexyl)dimethylamine hydrochloride, more polar diastereoisomer,
[4-(4-fluorobenzyloxymethyl)-1-phenylcyclohexyl]dimethylamine hydrochloride, less polar diastereoisomer, and
[4-(4-fluorobenzyloxymethyl)-1-phenylcyclohexyl]dimethylamine hydrochloride, more polar diastereoisomer,
optionally also in the form of their mixtures.

The substances according to the invention are active e.g. on the ORL1 receptor relevant in connection with various diseases, making them suitable as pharmaceutical active substances in pharmaceutical formulations. The invention therefore also provides pharmaceutical formulations containing at least one 4-hydroxymethyl-1-arylcyclohexylamine derivative.

In addition to at least one 4-hydroxymethyl-1-arylcyclohexylamine derivative according to the invention, the pharmaceutical formulations according to the invention optionally contain suitable additives and/or auxiliary substances, as well as excipients, fillers, solvents, diluents, colourants and/or binders, and can be administered as liquid dosage forms such as injectable solutions, drops or juices, or as semisolid dosage forms such as granules, tablets, pellets, patches, capsules, plasters or aerosols. The choice of auxiliary substances etc. and the amounts thereof to be used depend on whether the pharmaceutical formulation is to be administered by the oral, peroral, parenteral, intravenous, intraperitoneal, intradermal, intramuscular, intranasal, buccal, rectal or local route, for example to the skin, mucous membranes or eyes. Preparations suitable for oral administration take the form of tablets, dragees, capsules, granules, drops, juices and syrups, and preparations suitable for parenteral, topical and inhalational administration take the form of solutions, suspensions, readily reconstitutable dry preparations and sprays. 4-Hydroxymethyl-1-arylcyclohexylamine derivatives according to the invention in a depot, in dissolved form or in a plaster, optionally with the addition of skin penetration promoters, are suitable preparations for percutaneous administration. Dosage forms for oral or percutaneous administration can release the 4-hydroxymethyl-1-arylcyclohexylamine derivatives according to the invention with a delay. In principle, other active substances known to those skilled in the art can be added to the pharmaceutical formulations according to the invention.

The amount of active substance to be administered to the patient varies according to the patient's weight, the mode of administration, the indication and the severity of the disease. It is conventional to administer 0.005 to 1000 mg/kg, preferably 0.05 to 5 mg/kg, of at least one 4-hydroxymethyl-1-arylcyclohexylamine derivative according to the invention.

For all the above forms of the pharmaceutical formulations according to the invention, it can be advantageous for the pharmaceutical formulation to contain, in addition to at least one 4-hydroxymethyl-1-arylcyclohexylamine derivative, another active substance, especially an opioid and preferably a potent opioid, particularly morphine, or an anaesthetic, preferably hexobarbital or halothane.

One preferred form of the pharmaceutical formulation contains a 4-hydroxymethyl-1-arylcyclohexylamine derivative according to the invention as a pure diastereoisomer and/or enantiomer, as the racemate or as a non-equimolar or equimolar mixture of the diastereoisomers and/or enantiomers.

As seen in the introduction referring to the state of the art, the ORL1 receptor has been identified particularly in pain processes. Accordingly, 4-hydroxymethyl-1-aryl-cyclohexylamine derivatives according to the invention can be used to prepare a pharmaceutical formulation for the treatment of pain, especially acute, neuropathic or chronic pain.

The invention therefore also provides the use of a 4-hydroxymethyl-1-arylcyclohexylamine derivative according to the invention to prepare a pharmaceutical formulation for the treatment of pain, especially acute, visceral, neuropathic or chronic pain.

The invention therefore also provides the use of a 4-hydroxymethyl-1-arylcyclohexylamine derivative according to the invention to prepare a pharmaceutical formulation for the treatment of anxiety states, stress and stress-related syndromes, depression, epilepsy, Alzheimer's disease, senile dementia, general cognitive dysfunctions, learning and memory disorders (as a nootropic), withdrawal symptoms, alcohol and/or narcotic and/or pharmaceutical formulation abuse and/or dependence, sexual dysfunctions, cardiovascular diseases, hypotension, hypertension, tinnitus, pruritus, migraine, hearing difficulty, deficient intestinal motility, disturbed ingestion, anorexia, obesity, locomotor disturbances, diarrhoea, cachexia and urinary incontinence, or as a muscle relaxant, anticonvulsive or anaesthetic, or for coadministration in the case of treatment with an opioid analgesic or an anaesthetic, for diuresis or antinatriuresis, and anxiolysis, for the modulation of motor activity, for the modulation of neurotransmitter release and the treatment of associated neurodegenerative diseases, for the treatment of withdrawal symptoms and/or for reduction of the addiction potential of opioids.

It can be preferable, in one of the above uses, for a 4-hydroxymethyl-1-arylcyclohexylamine derivative used to be present as a pure diastereoisomer and/or enantiomer, as the racemate or as a non-equimolar or equimolar mixture of the diastereoisomers and/or enantiomers.

The invention also provides a method for the treatment, especially in one of the above-mentioned indications, of a non-human mammal or a human requiring a treatment for pain, especially chronic pain, by the administration of a therapeutically effective dose of a 4-hydroxymethyl-1-arylcyclohexylamine derivative according to the invention or a pharmaceutical formulation according to the invention.

The invention also provides a process for the preparation of the 4-hydroxymethyl-1-arylcyclohexylamine derivatives according to the invention, as illustrated in the description and Examples which follow. Particularly suitable processes are the two mentioned below as process I and process II for the preparation of a 4-hydroxymethyl-1-arylcyclohexylamine derivative according to the invention from appropriately substituted 4-aminocyclohexanones with subsequent steps, in which $R^1$, $R^2$, $R^3$ and $R^5$ are defined as indicated in compounds of formula I according to the invention, and $R^{01}$ and $R^{02}$ independently of one another are a protecting group or are defined as indicated for $R^1$ and $R^2$ in compounds of formula I according to the invention:

Process I:

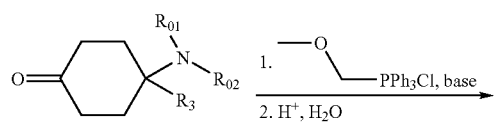

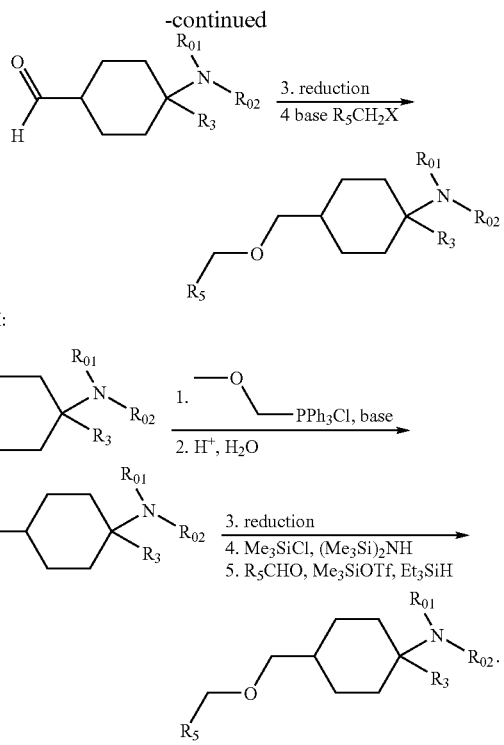

Process II:

In both processes, 4-aminocyclohexanone derivatives are reacted with methoxytriphosphonium chloride and a base, for example sodium hydride, and then with an aqueous acid, for example HCl, to give the corresponding aldehydes.

In process I, 4-aminocyclohexanecarbaldehyde derivatives are reduced with hydrogen using a reducing agent, for example a hydride such as sodium or lithium borohydride, sodium cyanoborohydride, sodium triacetoxyborohydride, diisobutylaluminium hydride, lithium tri(sec-butyl)borohydride (L-Selectride®) or lithium aluminium hydride, optionally in the presence of a Lewis acid, for example $ZnCl_2$, $Ni(OAc)_2$ or $CoCl_2$, or by catalytic hydrogenation on a noble metal, for example palladium or platinum, and then reacted with an alkylating agent:

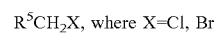 $R^5CH_2X$, where X=Cl, Br in the presence of a base, for example potassium tert-butylate, lithium or sodium hydride, potassium or sodium hydroxide, butyllithium, or another basic organometallic compound such as a Grignard reagent, for example ethylmagnesium chloride or bromide, to give the 4-hydroxymethyl-1-arylcyclohexylamine derivatives according to the invention.

In process II, 4-aminocyclohexanecarbaldehyde derivatives are reduced with hydrogen by adding a reducing agent, for example a hydride such as sodium or lithium borohydride, sodium cyanoborohydride, sodium triacetoxyborohydride, diisobutylaluminium hydride, lithium tri(sec-butyl)borohydride (L-Selectride®) or lithium aluminium hydride, optionally in the presence of a Lewis acid, for example $ZnCl_2$, $Ni(OAc)_2$ or $CoCl_2$, or by catalytic hydrogenation on a noble metal, for example palladium or platinum, to give the corresponding alcohols, and the alcohols are subsequently reacted with trimethylchlorosilane, hexamethyldisilazane and then an aldehyde $R^5CHO$, with the addition of trimethylsilyl triflate and triethylsilane, to give the 4-hydroxymethyl-1-arylcyclohexylamine derivatives according to the invention.

The preparation of suitable 4-aminocyclohexanones is known from the literature (Lednicer et al., J. Med. Chem. 23, 1980, 424-430; WO 0290317).

Isolation of the compounds according to the invention by column chromatography with silica gel as the stationary phase and ethyl acetate, methanol, ethyl acetate/methanol mixtures or ethyl acetate/diethyl ether mixtures as the solvent allows the diastereoisomers of different polarity to be separated. On the basis of their development time in the separation, these were characterized as the "least polar diastereoisomer" (shortest development time) to the "most polar diastereoisomer" (longest development time).

The invention is illustrated in greater detail below by means of Examples without implying a limitation.

EXAMPLES

The yields of the compounds prepared are not optimized.

All temperatures are uncorrected.

"Ether" denotes diethyl ether, "EE" denotes ethyl acetate, "DCM" denotes dichloromethane, "DMF" denotes dimethylformamide, "DMSO" denotes dimethyl sulfoxide and "THF" denotes tetrahydrofuran. "Equivalents" denotes quantity equivalents, "m.p." denotes melting point or melting range, "decomp." denotes decomposition, "RT" denotes room temperature, "abs." denotes absolute (anhydrous), "rac." denotes racemic, "conc." denotes concentrated, "min" denotes minutes, "h" denotes hours, "d" denotes days, "vol. %" denotes percent by volume, "wt. %" denotes percent by weight and "M" is the unit of concentration mol/l.

The stationary phase used for column chromatography was silica gel 60 (0.040-0.063 mm) from E. Merck, Darmstadt.

The thin layer chromatography experiments were carried out with precoated silica gel 60 F 254 HPTLC plates from E. Merck, Darmstadt.

The mixing proportions of solvents for chromatography experiments are always given in volume/volume.

Example 1

(4-Benzyloxymethyl-1-phenylcyclohexyl)dimethylamine hydrochloride, less polar diastereoisomer 4-Dimethylamino-4-phenylcyclohexanecarbaldehyde—
Method A:

Under argon, methoxymethyltriphenylphosphonium chloride (6.3 g, 18.4 mmol) was dissolved in DMF (25 ml), and sodium hydride (60 wt. % in mineral oil, 737 mg, 18.4 mmol) was added. A solution of 4-dimethylamino-4-phenyl-cyclohexanone (2.0 g, 9.2 mmol) in 25 ml of DMF was added dropwise over 30 min and the suspension was stirred for 3 d at RT. For the work-up, the suspension was poured slowly into 2 M HCl (50 ml) cooled with ice-water, stirred at RT for 2 h and then extracted with diethyl ether (5×25 ml) and EE (6×20 ml). The aqueous phase was then brought to pH 10-11 with 1 M NaOH and extracted with EE (5×20 ml). The combined extracts were dried with sodium sulfate, filtered and concentrated. The residue was 4-dimethylamino-4-phenylcyclohexanecarbaldehyde (2.0 g of brown oil) in a diastereoisomer ratio of 55:45 ($^1$H NMR).

4-Dimethylamino-4-phenylcyclohexanecarbaldehyde—
Method B:

Methoxymethyltriphenylphosphonium chloride (2.7 g, 8 mmol) was dissolved in abs. DMSO (5 ml) and THF (10 ml) under argon and cooled to <0° C. A solution of potassium tert-butylate (900 mg, 8 mmol) in THF (10 ml) was added dropwise and the mixture was then stirred for 15 min at 0° C. After heating to RT, a solution of 4-dimethylamino-4-phenyl-cyclohexanone (870 mg, 4 mmol) in THF (6 ml) was added dropwise and the mixture was stirred overnight. For the work-up, the reaction mixture was treated with water (5 ml) and 5.5 M HCl (15 ml), with ice-water cooling, and stirred. After 1 h it was extracted at RT with ether (10×20 ml). The aqueous phase was brought to pH 10 with 5 M NaOH and extracted with EE (5×15 ml). The combined extracts were dried, filtered and concentrated to give a 32:68 mixture of the diastereoisomers of 4-dimethylamino-4-phenylcyclohexanecarbaldehyde (850 mg of brown oil).

4-Dimethylamino-4-phenylcyclohexanecarbaldehyde—
Method C:

Method B was repeated in pure abs. THF, with analogous batch size, procedure and yield, to give a diastereoisomer ratio of 60:40.

(4-Dimethylamino-4-phenylcyclohexyl)methanol:

4-Dimethylamino-4-phenylcyclohexanecarbaldehyde (2.35 g, 10.2 mmol) was stirred in a mixture of 1 M NaOH (10.2 ml) and ethanol/water (2:1, 60 ml) for 30 min at RT under argon as inert gas. A solution of sodium borohydride (769 mg, 20.3 mmol) in water (40 ml) was then added dropwise at RT over 60 min and the mixture was stirred for 2 h. For the work-up, the ethanol was driven off under vacuum and the aqueous residue was extracted with EE (6×20 ml). The combined extracts were washed with saturated NaCl solution (2×20 ml), dried and concentrated. The resulting residue (2.2 g of brown oil) was a mixture of the two diastereoisomers of (4-dimethylamino-4-phenylcyclohexyl)methanol.

(4-Benzyloxymethyl-1-phenylcyclohexyl)dimethylamine hydrochloride, less polar diastereoisomer:

(4-Dimethylamino-4-phenylcyclohexyl)methanol (1.8 g, 7.7 mmol) was placed in abs. DMSO (10 ml), and a solution of potassium tert-butylate (1.73 g, 15.4 mmol) in DMSO (20 ml) was added dropwise over 15 min. The mixture was heated to 50° C. and stirred for 30 min, after which benzyl chloride (1.46 g, 11.6 mmol) in DMSO (10 ml) was added dropwise over 15 min. After stirring overnight at 50° C., water (20 ml) was added and the mixture was extracted with ether (3×30 ml) followed by DCM (3×30 ml). The combined extracts were washed with water (20 ml), dried, filtered and concentrated. The resulting residue (2.85 g) was heated to the reflux point with EE (30 ml) and filtered hot and the filtrate was kept overnight at 4° C. The solid which had precipitated out was filtered off with suction and dried (960 mg of a mixture of the diastereoisomeric target products), the mother liquor was concentrated to dryness and the resulting residue (1.37 g) was chromatographed on silica gel with ether to which an increasing amount of methanol was added. This gave 308 mg of the less polar diastereoisomer of (4-benzyloxymethyl-1-phenylcyclohexyl)dimethylamine, which was dissolved in 2-butanone (2 ml). The addition of chlorotrimethylsilane (129 µl) and water (9 µl) gave an oily residue, which yielded 258 mg of the corresponding hydrochloride after drying.

Example 2

(4-Benzyloxymethyl-1-phenylcyclohexyl)dimethylamine hydrochloride, more polar diastereoisomer As described for Example 1, 278 mg of the more polar diastereoisomer of (4-benzyloxymethyl-1-phenylcyclohexyl)dimethylamine were also obtained and this was converted analogously to 305 mg of the corresponding hydrochloride.

Example 3

[4-(4-Fluorobenzyloxymethyl)-1-phenylcyclohexyl]dimethylamine hydrochloride, less polar diastereoisomer As described for Example 1, 4-fluorobenzyl chloride (1.67 g, 11.6 mmol) was also reacted with 4-dimethylamino-4-phenylcyclohexyl)methanol (1.8 g, 7.7 mmol) and potassium tert-butylate (1.73 g, 15.4 mmol). Purification of the crude product (2.78 g) by chromatography gave 480 mg of the less polar diastereoisomer of [4-(4-fluorobenzyloxymethyl)-1-phenylcyclohexyl]dimethylamine and this was converted analogously to 348 mg of the corresponding hydrochloride.

Example 4

[4-(4-Fluorobenzyloxymethyl)-1-phenylcyclohexyl]dimethylamine hydrochloride, more polar diastereoisomer (4-Dimethylamino-4-phenylcyclohexyl)methanol (2.2 g, 9.4 mmol) was dissolved in abs. THF (25 ml), and hexamethyldisilazane (10.3 ml, 49.8 mmol) and chlorotrimethylsilane (2.35 ml, 25.1 mmol) were added at RT. After 18 h at RT, the mixture was evaporated to dryness under vacuum. The residue was taken up in ether (35 ml) and washed with 1.1 M $NaHCO_3$ solution (2×5 ml). The organic phase was diluted to 50 ml with ether, dried over sodium sulfate, filtered and concentrated. The resulting dimethyl(1-phenyl-4-trimethylsilanyloxymethylcyclohexyl)amine (2.4 g of brown oil) was used without further purification.

Under argon, 4-fluorobenzaldehyde (149 mg, 1.2 mmol) and dimethyl(1-phenyl-4-trimethylsilanyloxymethylcyclohexyl)amine (306 mg, 1 mmol) were dissolved in abs. DCM (20 ml) and cooled to 0° C. Trimethylsilyl triflate (387 µl, 2 mmol) was added dropwise at 0° C. and the mixture was stirred for 60 min at this temperature, after which triethylsilane (319 µl, 2 mmol) was added dropwise at 0° C. With slow heating to RT, the mixture was stirred overnight. For the work-up, DCM (10 ml) and 1 M NaOH (5 ml) were added and the mixture was stirred vigorously for 15 min. The organic phase was separated off, washed with 1 M NaOH (2×2 ml) and with water (1×2 ml), dried, filtered and concentrated. The residue was purified by chromatography on silica gel [40 g of silica gel 60; eluent: 600 ml of EE/MeOH (1:1) and 600 ml of MeOH/conc. $NH_3$ (400:1)]. The two diastereoisomers of [4-(4-fluorobenzyloxymethyl)-1-phenylcyclohexyl]dimethylamine were isolated (17 mg of less polar diastereoisomer (yellow oil) and 106 mg of more polar diastereoisomer (yellow oil)). 75 mg of the more polar diastereoisomer were dissolved in 2-butanone (2 ml), with heating, chlorotrimethylsilane (83.4 µl) was added dropwise at RT and the mixture was stirred for 2 h. The solvent was completely distilled off and the residue was covered with a layer of dry ether and mechanically detached from the wall of the flask. The resulting solid was filtered off with suction, washed with ether (4×2 ml) and dried to give 79 mg of the hydrochloride of the more polar diastereoisomer of [4-(4-fluorobenzyloxymethyl)-1-phenylcyclohexyl]-dimethylamine (greyish-white solid, m.p. 176-181° C.).

Studies on the Efficacy of the Compound According to the Invention:

The data acquired in the following assays and models are collated in Table 1.

Measurement of the ORL1 Binding

The cyclohexane derivatives of general formula I were studied in a receptor binding assay with $^3$H-nociceptin/Orphanin FQ using membranes of recombinant CHO-ORL1 cells. This test system was used according to the method presented by Ardati et al. (Mol. Pharmacol. 51, 1997, pp 816-824). The concentration of $^3$H-nociceptin/Orphanin FQ in these experiments was 0.5 nM. The binding assays were carried out with 20 mg of membrane protein per 200 µl of preparation in 50 mM Hepes, pH 7.4, 10 mM $MgCl_2$ and 1 mM EDTA. The binding to the ORL1 receptor was determined using 1 mg of WGA SPA beads (Amersham-Pharmacia, Freiburg) by incubation of the preparation for one hour at RT and subsequent measurement in a Trilux scintillation counter (Wallac, Finland). The affinity is given in Table 1 as the nanomolar $K_i$ value or as the % inhibition at c=1 µM.

Measurement of the µ Binding

The affinity for the human µ opiate receptor was determined in a homogeneous preparation in microtitre plates. For this purpose, dilution series of the particular substituted spirocyclic cyclohexane derivative to be tested were incubated for 90 minutes at room temperature with a receptor membrane preparation (15-40 µg of protein per 250 µl of incubation preparation) of CHO-K1 cells that express the human µ opiate receptor (RB-HOM receptor membrane preparation from NEN, Zaventem, Belgium), in the presence of 1 nmol/l of the radioactive ligand [$^3$H]-Naloxon (NET719, NEN, Zaventem, Belgium) and 1 mg of WGA SPA beads (wheat germ agglutinin SPA beads from Amersham/Pharmacia, Freiburg, Germany), in a total volume of 250 µl. The incubation buffer used was 50 mmol/l of Tris-HCl supplemented with 0.05 wt. % of sodium azide and 0.06 wt. % of bovine serum albumin. To determine the non-specific binding, 25 µmol/l of Naloxon were also added. When the ninety minutes of incubation time had elapsed, the microtitre plates were centrifuged for 20 minutes at 1000 g and the radioactivity was measured in a β counter (Microbeta-Trilux, PerkinElmer, Wallac, Freiburg, Germany). The percentage displacement of the radioactive ligand from its binding to the human µ opiate receptor at a test substance concentration of 1 µmol/l was determined and reported as the percentage inhibition (% inhibition) of the specific binding. In some cases the percentage displacement by different concentrations of the test compounds of general formula I was used to calculate the inhibitory concentrations $IC_{50}$, which effect a 50 percent displacement of the radioactive ligand. $K_i$ values for the test substances were obtained by conversion using the Cheng-Prusoff relationship.

Analgesia Study by the Mouse Tail Flick Test

The mice were individually placed in a test cage and the base of the tail was exposed to the focused thermal radiation from an electric lamp (tail flick type 50/08/1.bc, Labtec, Dr. Hess). The lamp intensity was adjusted so that the time between when the lamp was switched on and when the tail was suddenly flicked away (pain latency) was 3 to 5 seconds for the untreated mice. Before administration of the solutions containing the compound according to the invention, or the corresponding reference solutions, the mice were pretested twice within five minutes and the mean of these 5 measurements was calculated as the pretest mean.

The solutions of the compound of general formula I according to the invention, and the reference solutions, were then administered intravenously. The pain measurement was made 10, 20, 40 and 60 minutes after each intravenous administration. The analgesic action was determined as the increase in pain latency (% of the maximum possible antinociceptive effect) using the following formula:

$$[(T_1-T_0)/(T_2-T_0)] \times 100$$

where time $T_0$ is the latency time before administration, the time $T_1$ is the latency time after administration of the active substance combination, and the time $T_2$ is the maximum exposure time (12 seconds).

TABLE 1

| Example no. | ORL1 $K_i$ [nM] or % inhibition [1 μM] | μ $K_i$ [nM] or % inhibition [1 μM] | Tail flick (mouse, i.v.) $ED_{50}$ [mg/kg] or % inhibition (dose [mg/kg]) |
| --- | --- | --- | --- |
| 1 | 26 | 4.7 | 87 |
| 2 | 370 | 78% | 96 |
| 3 | 21 | 8.9 | |
| 4 | 250 | 40 | |

Example 5

Parenteral Solution of a 4-hydroxymethyl-1-arylcyclohexylamine Derivative According to the Invention 1 g of one of the 4-hydroxymethyl-1-arylcyclohexylamine derivatives according to the invention, in this case the compound of Example 1, is dissolved at room temperature in 1 l of water for injection and then adjusted to isotonic conditions by adding anhydrous glucose for injection.

What is claimed is:

1. A 4-hydroxymethyl-1-arylcyclohexylamine compound corresponding to formula I:

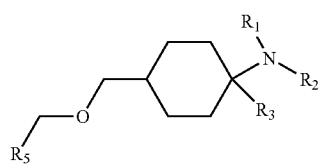

wherein, $R^1$ and $R^2$ independently of one another are H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted, or the radicals $R^1$ and $R^2$ together form a ring and are $CH_2CH_2OCH_2CH_2$, $CH_2CH_2NR^6CH_2CH_2$ or $(CH_2)_{3-6}$, $R^6$ being H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted;

$R^3$ is $C_{3-8}$-cycloalkyl, which is saturated or unsaturated, branched or unbranched and monosubstituted, polysubstituted or unsubstituted; aryl or heteroaryl, each of which is unsubstituted, monosubstituted or polysubstituted; or aryl, $C_{3-8}$-cycloalkyl or heteroaryl bonded via a saturated or unsaturated, branched or unbranched and substituted or unsubstituted $C_{1-4}$-alkyl group, each of which is unsubstituted, monosubstituted or polysubstituted; and $R^5$ is $C_{3-8}$-cycloalkyl, aryl or heteroaryl, each of which is unsubstituted, monosubstituted or polysubstituted; or $—CH_2R^{12}$, $—CH_2—CH_2R^{12}$ or $—CH_2—CH_2—CH_2R^{12}$, $R^{12}$ being $C_{3-8}$-cycloalkyl, aryl or heteroaryl, each of which is unsubstituted, monosubstituted or polysubstituted, or a salt thereof with a physiologically tolerated acid, or a solvate thereof.

2. The compound of claim 1, wherein said compound is present in the form of a pure enantiomer or pure diastereoisomer.

3. The compound of claim 1, wherein said compound is present in the form of a mixture of stereoisomers.

4. The compound of claim 1, wherein said compound is present in the form of a racemic mixture.

5. A 4-hydroxymethyl-1-arylcyclohexylamine compound according to claim 1, wherein $R^1$ and $R^2$ independently of one another are H; or $C_{1-8}$-alkyl which is saturated or unsaturated, branched or unbranched and monosubstituted, polysubstituted or unsubstituted, or the radicals $R^1$ and $R^2$ together form a ring and are $CH_2CH_2OCH_2CH_2$, $CH_2CH_2NR^6CH_2CH_2$ or $(CH_2)_{3-6}$, $R^6$ being H; or $C_{1-8}$-alkyl which is saturated or unsaturated, branched or unbranched and monosubstituted, polysubstituted or unsubstituted.

6. A 4-hydroxymethyl-1-arylcyclohexylamine compound according to claim 1, wherein $R^1$ and $R^2$ independently of one another are H; or $C_{1-4}$-alkyl which is saturated or unsaturated, branched or unbranched and monosubstituted, polysubstituted or unsubstituted, provided $R^1$ and $R^2$ are not both H, or the radicals $R^1$ and $R^2$ together form a ring and are $(CH_2)_{4-5}$.

7. A 4-hydroxymethyl-1-arylcyclohexylamine compound according to claim 1, wherein $R^1$ and $R^2$ independently of one another are methyl or ethyl, or the radicals $R^1$ and $R^2$ together form a ring and are $(CH_2)_5$.

8. A 4-hydroxymethyl-1-arylcyclohexylamine compound according to claim 1, wherein $R^1$ and $R^2$ independently of one another are $CH_3$ or H, provided $R^1$ and $R^2$ are not both H.

9. A 4-hydroxymethyl-1-arylcyclohexylamine compound according to claim 1, wherein $R^3$ is $C_{3-8}$-cycloalkyl, aryl or heteroaryl, each of which is unsubstituted, monosubstituted or polysubstituted; or aryl, $C_{3-8}$-cycloalkyl or heteroaryl bonded via a saturated or unsaturated, unbranched and substituted or unsubstituted $C_{1-2}$-alkyl group, each of which is unsubstituted, monosubstituted or polysubstituted.

10. A 4-hydroxymethyl-1-arylcyclohexylamine compound according to claim 1, wherein $R^3$ is cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, each of which is unsubstituted, monosubstituted or polysubstituted; or a $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated unbranched $C_{1-2}$-alkyl group, each of which is unsubstituted, monosubstituted or polysubstituted.

11. A 4-hydroxymethyl-1-arylcyclohexylamine compound according to claim 1, wherein $R^3$ is phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, each of which is unsubstituted, monosubstituted or polysubstituted; or phenyl, furyl or thiophenyl bonded via a saturated unbranched $C_{1-2}$-alkyl group, each of which is unsubstituted, monosubstituted or polysubstituted.

12. A 4-hydroxymethyl-1-arylcyclohexylamine compound according to claim 1, wherein $R^3$ is phenyl, thiophenyl, pyridyl or benzyl, each of which is substituted or unsubstituted.

13. A 4-hydroxymethyl-1-arylcyclohexylamine compound according to claim 1, wherein R3 is phenyl.

14. A 4-hydroxymethyl-1-arylcyclohexylamine compound according to claim 1, wherein $R^5$ is $C_{3-8}$-cycloalkyl, aryl or heteroaryl, each of which is unsubstituted, monosubstituted or polysubstituted.

15. A 4-hydroxymethyl-1-arylcyclohexylamine compound according to claim 1, wherein $R^5$ is cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each of which is unsubstituted, monosubstituted or polysubstituted.

16. A 4-hydroxymethyl-1-arylcyclohexylamine compound according to claim 1, wherein $R^5$ is cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each of which is unsubstituted, monosubstituted or polysubstituted.

17. A 4-hydroxymethyl-1-arylcyclohexylamine compound corresponding to formula I:

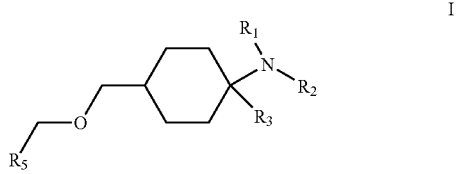

wherein $R^1$ and $R^2$ independently of one another are H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted, or the radicals $R^1$ and $R^2$ together form a ring and are $CH_2CH_2OCH_2CH_2$, $CH_2CH_2NR^6CH_2CH_2$ or $(CH_2)_{3-6}$, $R^6$ being H; $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is monosubstituted, polysubstituted or unsubstituted; or aryl, $C_{3-8}$-cycloalkyl or heteroaryl bonded via $C_{1-3}$-alkyl, each of which is monosubstituted, polysubstituted or unsubstituted;

$R^3$ is $C_{1-8}$-alkyl or $C_{3-8}$-cycloalkyl, each of which is saturated or unsaturated, branched or unbranched and monosubstituted, polysubstituted or unsubstituted; aryl or heteroaryl, each of which is unsubstituted, monosubstituted or polysubstituted; or aryl, $C_{3-8}$-cycloalkyl or heteroaryl bonded via a saturated or unsaturated, branched or unbranched and substituted or unsubstituted $C_{1-4}$-alkyl group, each of which is unsubstituted, monosubstituted or polysubstituted; and $R^5$ is $-CH_2R^{12}$, $-CH_2-CH_2R^{12}$ or $-CH_2-CH_2-CH_2R^{12}$, $R^{12}$ being $C_{3-8}$-cycloalkyl, aryl or heteroaryl, each of which is unsubstituted, monosubstituted or polysubstituted, or a salt thereof with a physiologically tolerated acid, or a solvate thereof.

18. A 4-hydroxymethyl-1-arylcyclohexylamine compound according to claim 17, wherein $R^5$ is $-CH_2R^{12}$ or $-CH_2-CH_2R^{12}$.

19. A 4-hydroxymethyl-1-arylcyclohexylamine compound according to claim 17, wherein $R^5$ is $-CH_2R^{12}$.

20. A 4-hydroxymethyl-1-arylcyclohexylamine compound according to claim 17, wherein $R^{12}$ is cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each of which is unsubstituted, monosubstituted or polysubstituted.

21. A 4-hydroxymethyl-1-arylcyclohexylamine compound according to claim 17, wherein
$R^{12}$ is cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each of which is unsubstituted, monosubstituted or polysubstituted.

22. A 4-hydroxymethyl-1-arylcyclohexylamine compound, wherein said compound is selected from the group consisting of:
(4-benzyloxymethyl-1-phenylcyclohexyl)dimethylamine hydrochloride, less polar diastereoisomer,
(4-benzyloxymethyl-1-phenylcyclohexyl)dimethylamine hydrochloride, more polar diastereoisomer,
[4-(4-fluorobenzyloxymethyl)-1-phenylcyclohexyl]dimethylamine hydrochloride, less polar diastereoisomer, and
[4-(4-fluorobenzyloxymethyl)-1-phenylcyclohexyl]dimethylamine hydrochloride, more polar diastereoisomer, or a mixture of any of the foregoing.

23. A pharmaceutical formulation comprising as an active ingredient a pharmaceutically effective amount of at least one 4-hydroxymethyl-1-arylcyclohexylamine compound according to claim 1 and a pharmaceutically acceptable carrier or adjuvant.

24. A method of alleviating pain in a mammal, said method comprising administering to said mammal an effective pain alleviating amount of a 4-hydroxymethyl-1-arylcyclohexylamine compound according to claim 1.

25. The method of claim 24 wherein said pain is acute, visceral, neuropathic or chronic pain.

26. A method of treating anxiety, said method comprising administering a pharmaceutically effective amount of a 4-hydroxymethyl-1-arylcyclohexylamine compound according to claim 1.

27. A process for preparing a 4-hydroxymethyl-1-arylcyclohexylamine compound according to claim 1, comprising:
reducing a 4-aminocyclohexanecarbaldehyde compound with a reducing agent and reacting with an alkylating agent in the presence of a base, wherein said alkylating agent is $R^5CH_2X$, wherein where X is Cl or Br.

28. The process of claim 27, wherein said reducing agent is sodium borohydride.

29. The process of claim 27, wherein said base is potassium tert-butylate.

30. The process of claim 27, further comprising a preliminary step of reacting a 4-aminocyclohexanone compound with methoxytriphosphonium chloride and a base, and then with an aqueous acid.

31. The process of claim 30, wherein said base which is reacted with said aminocyclohexanone compound is sodium hydride.

32. The process of claim 30, wherein said aqueous acid is HCl.

33. A process for preparing a 4-hydroxymethyl-1-arylcyclohexylamine compound according to claim 1, comprising:
reducing a 4-aminocyclohexanecarbaldehyde compound with a reducing agent to yield the corresponding alcohol, and
reductively etherifying the alcohol with trimethylchlorosilane, hexamethyldisilazane and then an aldehyde, with the addition of trimethylsilyl triflate and triethylsilane, wherein said aldehyde is R5CHO.

34. The process of claim 33, wherein said reducing agent is sodium borohydride.

35. The process of claim 33, further comprising a preliminary step of reacting a 4-aminocyclohexanone compound with methoxytriphosphonium chloride and a base, and then with an aqueous acid.

36. The process of claim 33, wherein said base which is reacted with said aminocyclohexanone compound is sodium hydride.

37. The process of claim 33, wherein said aqueous acid is HCl.

* * * * *